United States Patent [19]
Kronner

[11] Patent Number: 5,817,110
[45] Date of Patent: Oct. 6, 1998

[54] ABDOMINAL INCISION SUTURING APPARATUS

[76] Inventor: Richard F. Kronner, 1443 Upper Cleveland Rapids Rd., Roseburg, Oreg. 97470

[21] Appl. No.: 851,878

[22] Filed: May 6, 1997

[51] Int. Cl.⁶ ..................................................... A61B 17/04
[52] U.S. Cl. ......................... 606/148; 606/147; 606/149; 606/139; 606/213
[58] Field of Search ................................... 606/139, 147, 606/148, 149, 213, 223

[56] References Cited

U.S. PATENT DOCUMENTS

| | | |
|---|---|---|
| 377,160 | 1/1888 | Hunter . |
| 818,152 | 4/1906 | Edwards . |
| 1,110,468 | 9/1914 | Turner . |
| 1,377,359 | 5/1921 | Littlejohn . |
| 3,116,707 | 1/1964 | Newman . |
| 3,160,157 | 12/1964 | Chisman . |
| 4,527,564 | 7/1985 | Eguchi et al. . |
| 4,586,926 | 5/1986 | Osborne . |
| 5,059,207 | 10/1991 | Shah . |
| 5,112,344 | 5/1992 | Petros . |
| 5,336,239 | 8/1994 | Gimpelson . |
| 5,578,044 | 11/1996 | Gordon et al. .......................... 606/139 |
| 5,613,975 | 3/1997 | Christy ..................................... 606/139 |
| 5,626,588 | 5/1997 | Sauer et al. ............................. 606/139 |
| 5,632,752 | 5/1997 | Buelna .................................... 606/139 |

FOREIGN PATENT DOCUMENTS 309633  4/1929  United Kingdom .

OTHER PUBLICATIONS

Core Dynamics, Inc., Maciol Laparoscopic Suture Needle Set product brochure, Copyright 1995, 1996 Medical Internet Communications, Inc., Core Dynamics, Inc., 11222–4 St. Johns Industrial Parkway, Jacksonville, FL. 32246, 3 pages.

Automated Medical Products Corp. DEEP SUTURE Mis Fascial Suturing Device product brochure, 2 pages, Automated Medical Products Corporation, 2315 Broadway, New York, NY 10024.

UNIMAR, J–Needle Suturing Needle, product brochure, 1 page–UNIMAR, Inc., P.O. Box 647, Wilton, CT 06897.

General Surgery & Laparoscopy News Feb. 1996, Advertising Supplement, "Sages Product Showcase", pp. 33, 34.

*Primary Examiner*—Gary Jackson
*Attorney, Agent, or Firm*—Edward B. Anderson; Gregory T. Kavounas

[57] ABSTRACT

An abdominal incision suturing apparatus includes a guide element that is inserted and maintained in an abdominal incision by a guide handle. The guide element has a passage for receiving slidably the shaft of a reverse needle. The shaft can be moved axially and rotationally with respect to the guide element by a shaft handle. The reverse needle has a needle at the distal end of the shaft, with a pointed end and an eye for receiving a suture. The guide element defines a sheath for receiving the pointed end of the needle. The guide element and the reverse needle together present a substantially airtight surface for maintaining the pneumoperitoneum pressure in a cannula site incision. Further, the guide element includes markings on its surface, for the user to monitor the depth of insertion via a laparoscope. The shaft handle has a specially shaped groove, and the guide element has an internal pin that protrudes into the groove. The pin thus confines the reverse needle to axial and rotational movement between four consecutive positions with respect to the guide element. The four positions correspond to the pointed end being (1) sheathed, (2) unsheathed and in line with the guide element, (3) laterally spaced from, and (4) laterally adjacent to the guide element for puncturing. A locking mechanism further immobilizes the reverse needle in selected positions. An unlocking mechanism releases the needle for movement.

28 Claims, 11 Drawing Sheets

Fig. 6 M

ABDOMINAL INCISION SUTURING APPARATUS

BACKGROUND OF THE INVENTION

1. Field of the Invention

The present invention relates to the field of suturing devices for suturing abdominal incisions, and in particular to such devices for suturing a cannula site incision.

2. Description of Related Art

Suturing an incision after abdominal surgery involves placing sutures through the abdominal wall surrounding the incision. The sutures should pass through all the raw layers of the abdominal wall, except the skin, to prevent abdominal viscera from being later trapped in the deep part of the sutured incision. These layers are not easy to access where there is only a small skin opening, as is the case with a small incision associated with a cannula tract.

The risk of injury to abdominal viscera is mitigated by using a reverse or j-shaped needle, as is taught in U.S. Pat. No. 5,336,239 to Gimpelson. A reverse needle has an elongated shaft, with a pointed end that is reversed, in that it points outward from the abdominal cavity. An abdominal wall can thus be punctured by a motion of pulling the reverse needle away from the abdomen. Moreover, the reverse needle has an eye near the pointed end, for threading a suture. This further enables manipulating the thread about the incision and within the cavity by simply manipulating the shaft of the needle, as shown in FIGS. 3A–3F of Gimpelson.

A limitation of reverse needles is in orienting the needle during use and in extracting them from an incision that can be as small as a laparoscope cannula port. Indeed, if the pointed end of the needle is not aligned with the incision in advance, an extraction attempt can result in an unnecessary puncture to abdominal layers. Gimpelson addresses this limitation by providing an optional bell that can slide along the cylindrical shaft and cap the pointed end. The bell does not provide a satisfactory solution. Indeed, during suturing, the user will have to keep the bell from sliding through the incision into the cavity. After suturing, the user must use the bell to cap the pointed end which, however, is completely within the cavity. As seen in FIG. 3G of Gimpelson, the bell is too short for that purpose. Indeed, the user must reach within the cavity to manipulate the bell onto the pointed end; and if he misses, the bell will slide along the shaft past the pointed end. Once the bell is in the cavity, it will be irretrievable, and the pointed end will have to be extracted uncapped.

Another solution to this problem is implemented by a device called DEEPSUTURE™ of Automated Medical Products Corp. An elongated post supports two parallel needles on wings, thus forming a double reverse needle. The wings can be deployed laterally with respect to the post, to space the needles from it. When the wings are retracted, the needles are received into corresponding channels in the post, so as not to interfere with extracting the post from a small incision. A similar device has a J-shaped needle eccentrically positioned in a sleeve. The needle is rotatable between a position in which the point is next to the sleeve to a position in which the point is spaced from the sleeve. A problem with these devices arise from the risk of inadvertent needle deployment during axial movement of the post or sleeve, which again can result in unnecessary puncture of abdominal wall layers.

It is desirable to have a suturing device that does not suffer from any of these limitations.

SUMMARY OF THE INVENTION

The present invention provides an abdominal incision suturing apparatus that overcomes these problems of the prior art. The apparatus includes a guide element that is inserted and maintained in an abdominal incision by a guide handle. The guide element has a passage for receiving slidably the shaft of a reverse needle. The reverse needle has a needle at the distal end of the shaft, with a pointed end and an eye for receiving a suture. The shaft can be moved axially and rotationally with respect to the guide element by a shaft handle. The shaft handle preferably includes a knob, with an arrow for indicating the position of the needle.

In a preferred embodiment of the invention, the guide element defines a sheath for receiving the pointed end of the needle. The guide element and the reverse needle together present a substantially airtight surface to maintain the pneumoperitoneum pressure during use. Further, the guide element includes markings on its surface, for the user to monitor the depth of insertion via a laparoscope.

The shaft handle has a specially shaped groove, and the guide element has an internal pin that protrudes into the groove. The pin thus confines the reverse needle to axial and rotational movement between four consecutive positions with respect to the guide element. The four positions correspond to the pointed end being (1) sheathed, (2) unsheathed and in line with the guide element, (3) laterally spaced from the guide element, and (4) laterally adjacent to the guide element (for puncturing). A locking mechanism immobilizes the reverse needle in selected positions so that the orientation of the needle can be controlled by the handle. An unlocking mechanism releases the reverse needle for the above described movement.

It can be seen that such a suturing apparatus has several beneficial features. It allows suturing without the user having to reach within the abdominal cavity. The arrow on the knob facilitates aiming of the pointed end for puncturing holes. The sheath allows the pointed end to be stowed, so that the apparatus can be withdrawn from the incision safely. The locking mechanism prevents the pointed end from being deployed inadvertently during that time. These and other features of the present invention will be apparent from the preferred embodiment described in the following detailed description and illustrated in the accompanying drawings.

DETAILED DESCRIPTION OF THE PREFERRED EMBODIMENT

As has been mentioned, the invention provides a surgical apparatus for suturing an incision in an abdominal wall, that is also known as an abdominal incision suturing apparatus. FIGS. 1–5 illustrate suturing apparatus 20 made according to the invention.

Apparatus 20 includes a reverse needle 22 which is also referred to as a J-shaped suture manipulating device. Reverse needle 22 includes an elongated shaft 24, that has a proximal end 26, a distal end 28, and is preferably cylindrical. Reverse needle 22 additionally includes a needle 30 with a base end 32 and a pointed end 34. The pointed end is sharp enough for puncturing an abdominal wall, but it does not need to be any sharper than that, because it is not intended to be used for puncturing the skin. Needle 30 is adapted for receiving a suture by having an eye 36 near pointed end 34.

Figure 1:
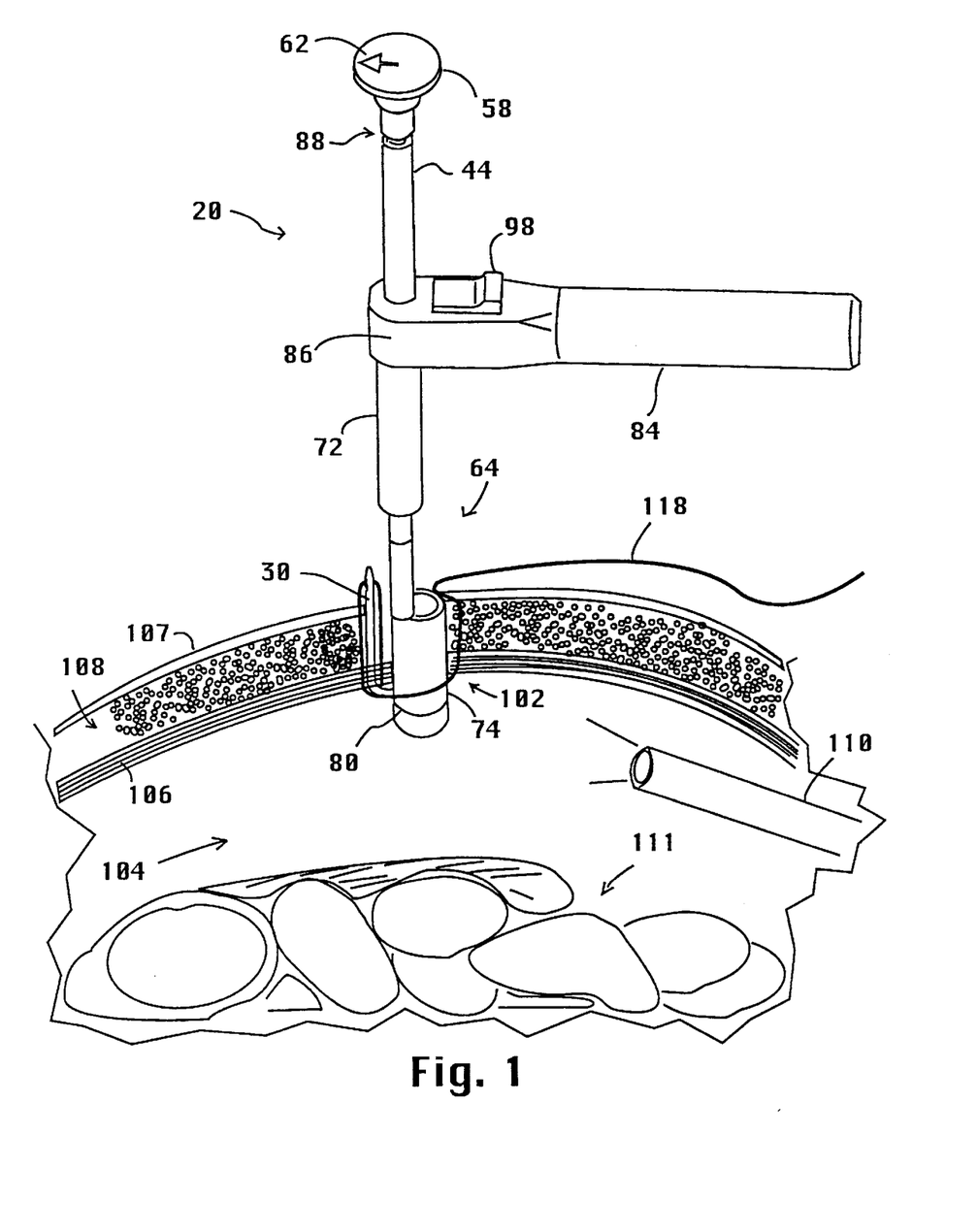
FIG. 1 is an isometric view of the preferred embodiment of an abdominal incision suturing apparatus according to the invention during suturing of a cannula incision.

The reverse needle further includes what is referred to as a support member 38 for supporting base end 32 of needle 30 on distal end 28 of shaft 24. As can be seen in FIG. 1, the needle is supported adjacent to and laterally spaced from the shaft. The needle is generally shorter than the shaft, and the pointed end points in the general direction of the proximal end of the shaft. It is preferred that the shaft, support member, and needle are integrally formed by shaping suitably one segment of stainless steel wire.

Proximal end 26 of shaft 24 is adapted for manipulating the location and orientation of distal end 28, and thus also the position of the pointed end 34 of needle 30. The proximal end of the shaft is adapted for attachment to a shaft handle 40. Shaft handle 40 (which is also known as shaft handle means) has an oblong cylindrical plunger 44, with a shaft end 46 and a user end 48. Plunger 44 has a radius larger than that of shaft 24. Shaft end 46 of the plunger has a first, axial opening 50 for receiving proximal end 26 of the shaft with the center axis of the shaft aligned with that of the plunger. Shaft end 46 also has a second, radial opening 52 perpendicular to the first opening for receiving a set screw 54. The shaft includes a circumferential bore 56 near the proximal end. One end of bore 56 receives set screw 54. The set screw secures the shaft to the shaft handle so that the reverse needle is movable by movement of the shaft handle.

It is preferred that the shaft handle includes, at the user end, a knob 58 which further presents a ridged surface 60 for secure grasping. It is also preferred that the knob includes a demarcation such as arrow 62 on the back side, shown in FIG. 1. The demarcation indicates the orientation of needle 30 with respect to knob 58.

Figure 2:
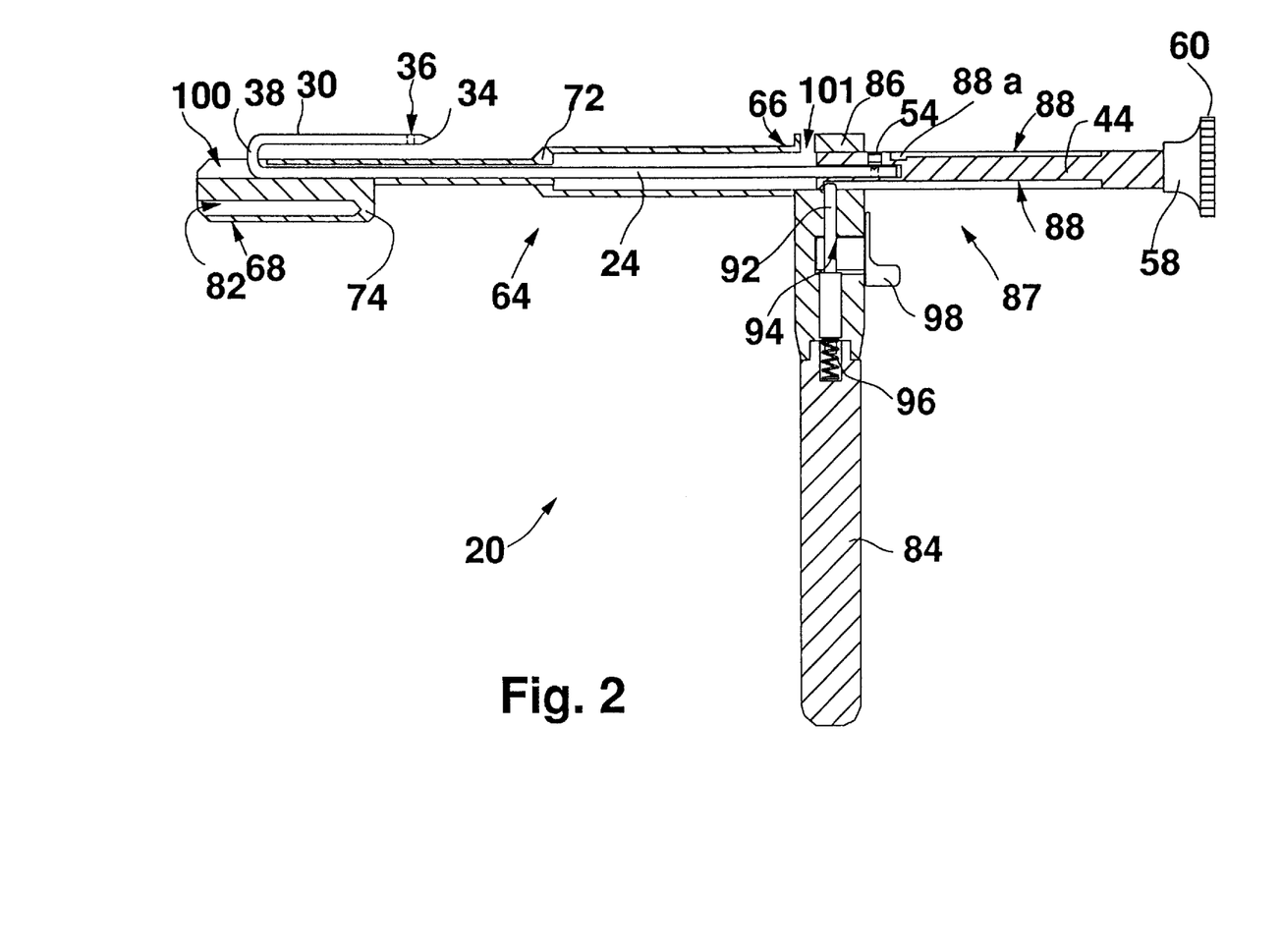
FIG. 2 is a cross sectional view of the suturing apparatus of FIG. 1.
Figure 5:
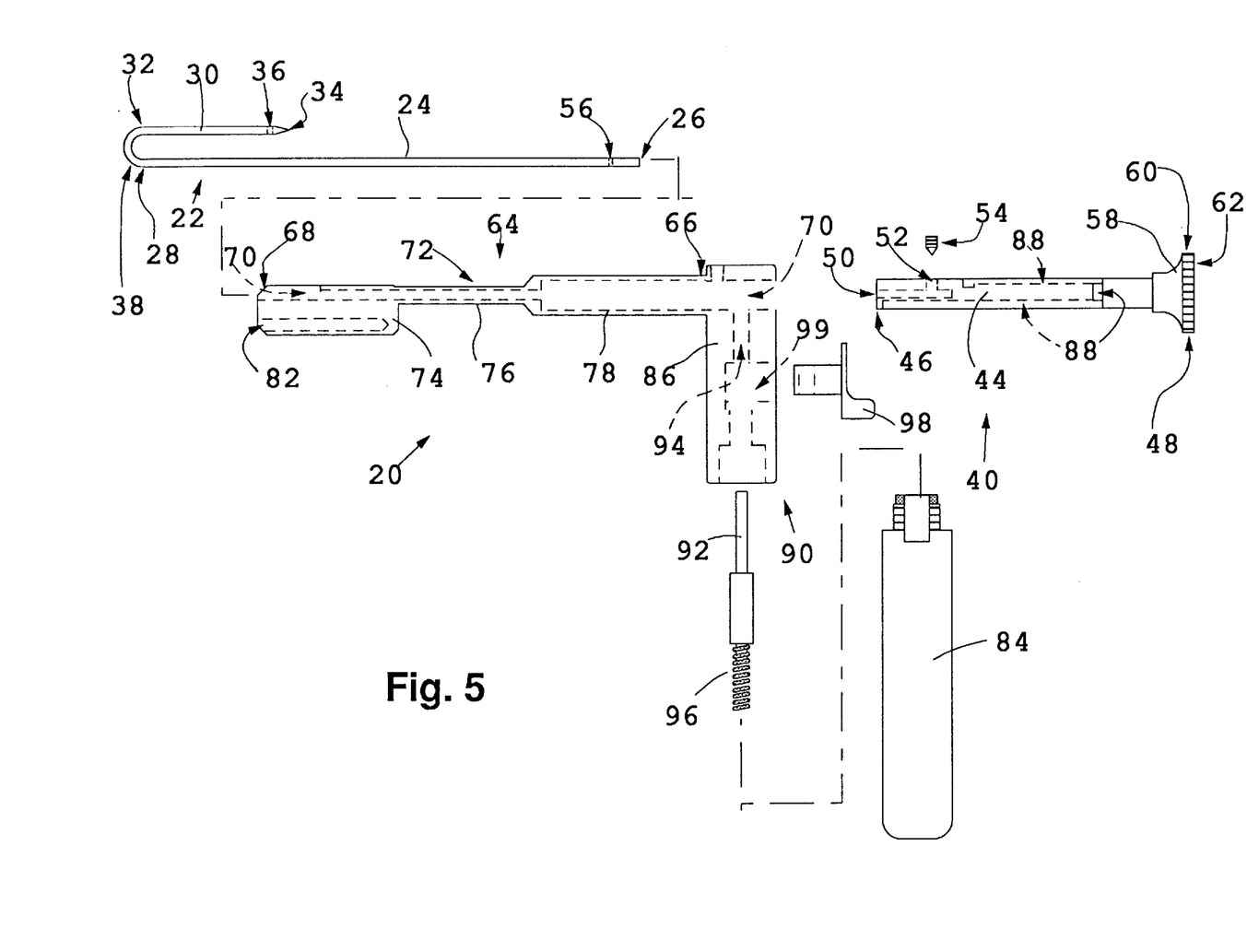
FIG. 5 is an exploded sectional view of the components of the suturing apparatus of FIG. 1.

Referring particularly to FIGS. 2 and 5, apparatus 20 further includes a guide element 64 with a proximal end 66 and a distal end 68. The guide element has a distal end adapted for insertion into an abdominal wall incision, and has a passage 70 extending between the proximal end and the distal end. Shaft 24 of the reverse needle is received in passage 70, with the distal end 28 of the shaft associated with the distal end 68 of the guide element.

Guide element 64 preferably includes a sleeve 72 in combination with a plug 74, as seen in FIGS. 1, 2 and 5. Sleeve 72 is generally tubular, with the hollow interior forming passage 70. It is preferred that the sleeve consists of two coaxial cylindrical sections 76, 78 that are joined sequentially. Intermediate section 76 is also attached to the plug, and has a reduced diameter, being only as thick as it needs to be to contain the shaft. By being thin, it permits the skin to be pulled over the plug during suturing, so as to avoid enlarging the skin wound unnecessarily. Upper section 78 has an internal diameter equal to that of the outer diameter of plunger 44 of shaft handle 40. Therefore, the upper section admits both the needle shaft and the user end of the shaft handle.

Passage 70 also traverses plug 74. The portion of the passage in the plug is preferably cylindrical, and has an inner diameter equal to the outer diameter of shaft 24. The shaft fits matingly within that portion of the passage. The guide element therefore presents a substantially airtight surface at the distal end, for maintaining the pneumoperitoneum pressure within the abdominal cavity. This further allows use of a laparoscope during suturing.

The outside distal end of the plug is preferably beveled for easy insertion into an incision. Plug 74 also includes gauge means for indicating the depth of insertion of guide element 64 in the incision, when the distal end is viewed by a laparoscope. In the preferred embodiment the gauge means is a depth indicator 80, located a short distance in from the distal end of the guide element. The depth indicator is implemented as a circumferential groove extending circumferentially around the plug.

It is preferred that the plug be of a substantially cylindrical shape for easy rotation within and sealing of the incision. Passage 70 extends eccentrically through the plug. This enables the needle to be moved advantageously from a position in line with the plug to a position spaced laterally from the plug by rotation of the shaft handle, for the diverse functions that are explained below.

Plug 74 includes a sheath 82 suitable for receiving pointed end 34 of the needle for stowage. The sheath is defined by a closed-ended opening in the structure of the plug at the distal end, as shown in FIG. 2. It is preferred that the opening be deep enough to accommodate much of the length of the needle. The pointed end is moved into the sheath from a position in line with the plug.

Apparatus 20 further includes a guide handle 84 for supporting the guide element manually, and is otherwise known as guide handle means. In the preferred embodiment, the guide handle is connected to upper section 78 of the sleeve by a connector 86. The user can thus hold the guide handle to maintain the guide element stationary with respect to the incision, and move the knob axially and rotationally with respect to the guide handle and the sleeve, and thereby moving the pointed end of the needle with respect to the plug.

The apparatus optionally and preferably also includes a movement confining means 87 for limiting the range of movement of the shaft relative to the guide element. It will be apparent that such movement corresponds to movement of the knob, plunger, shaft, support member, needle or its pointed end with respect to any of the plug, sleeve, guide element, connector or guide handle.

In the preferred embodiment, movement confining means 87 includes a specially shaped groove 88 formed on the outer surface of plunger 44 of the shaft handle, in conjunction with a lock assembly 90 that is implemented within connector 86. The plunger has a larger radius than the shaft in order to accommodate the groove. As seen in FIGS. 2–5, lock assembly 90 includes an internal pin 92 that is slidably received in an opening 94 of the connector. The pin protrudes through the opening, and is received in groove 88 of the plunger. The plunger can move only along a path that maintains the pin in the groove. The shape of the groove thus dictates the range of allowable movement of the shaft and needle relative to the guide element.

The groove is linear, which means that the shaft is confined to linear movement with respect to the guide element, and the needle can be placed in specific positions with respect to the guide element. Each such needle position corresponds to a position of the pin with respect to the groove. The shape of linear groove 88 is such that it permits the needle to be moved:

a) axially between a first position in the sheath (where it is locked by the position of pin 92 in recess 88a) and a second position outside the sheath and in line with the guide element, as determined by groove section 88b;

b) rotationally between the second position and a third position spaced laterally from the guide element, as determined by groove section 88c; and c) axially between the third position and a fourth position laterally adjacent to the guide element, as determined by groove section 88d.

Figure 3:
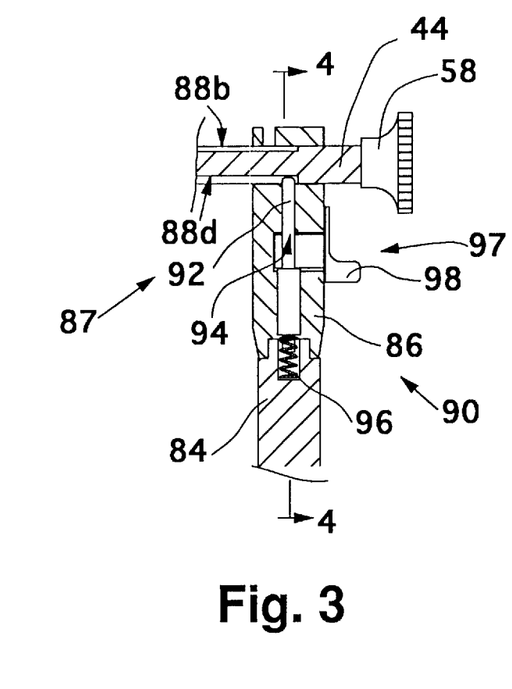
FIG. 3 is a cross section showing the detail of the movement confining means of the suturing apparatus of FIG. 1.
Figure 4:
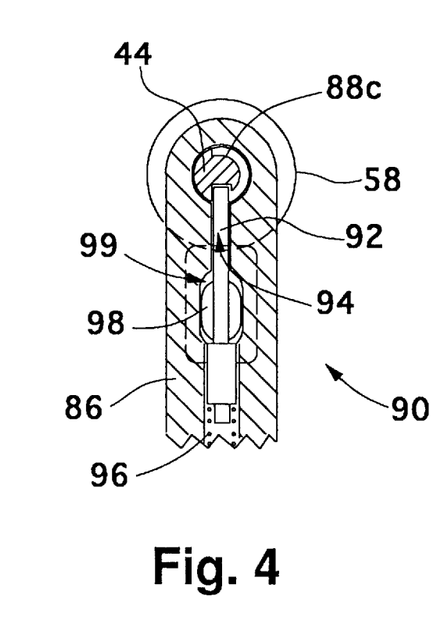
FIG. 4 is a cross section taken across line 4—4 of FIG. 3.

FIGS. 3 and 4 show the pin in groove section 88d when the pointed end of the needle is in the third position. FIG. 3 shows upper section 88b and lower section 88d of the groove. The upper section represents allowable axial motion between the first and the second positions. The lower portion represents allowable axial motion between the third and the fourth positions. FIG. 4 shows arcuate portion 88c, which represents allowable rotational motion from the second to the third position.

The movement confining means further confines movement of the shaft with respect to the guide element. The depth of groove 88 is not uniform along its length. The groove depth changes abruptly i.e. discontinuously, at points where it is desired to further limit movement, such as the point where the pointed end of the needle is received within the sheath. A spring 96 biases the pin through the opening and towards the plunger. The pin is captured in a deeper part of the groove, and thus further confines the movement of the plunger and needle.

An unlocking mechanism 97 consists of a manually slidable key 98 received in an enlarged channel 99. Key 98 worlds against the force of a spring 96 to draw pin 92 slightly away from the shaft handle, but never fully out of groove 88. As is seen in the drawings, recess 88a and section 88d are deeper than sections 88b and 88c. Key 98 is used to release pin 92 from recess 88a or to return the pin into section 88c from 88d. Once the pin is in section 88d it can only travel in that section, unless key 98 is used.

Groove section 88d is longer than section 88b. Accordingly, plug 74 additionally has a slotted opening 100 for allowing support member 38 to be received in the plug, as the needle is being moved from the third position to the fourth position. As seen in FIGS. 1 and 2, the fourth position is when plunger 44 of the shaft handle has been pulled back to the point where pin 92 has reached the farthest end of groove 88 and the needle point extends beyond the proximal end of the plug. Also, when the needle is in the fourth position, set screw 54 is exposed for access.

All components of the apparatus can be made from stainless steel for long life. The apparatus can thus be steam autoclavable. Additionally, as seen in FIG. 2, an irrigation port 101 on top of connector 86 permits irrigation of the internal passages of connector 86 when the connection is disassembled.

A method is now described for use of the preferred embodiment of the surgical apparatus of the invention in suturing an abdominal incision with reference to FIGS. 6A–6M. It is assumed that a pneumoperitoneum pressure has been established within the abdomen, which has distanced the abdominal wall from the viscera, and a laparoscope is positioned for internal viewing of the incision site. The pneumoperitoneum pressure is maintained through the suturing procedure.

Figure 6:
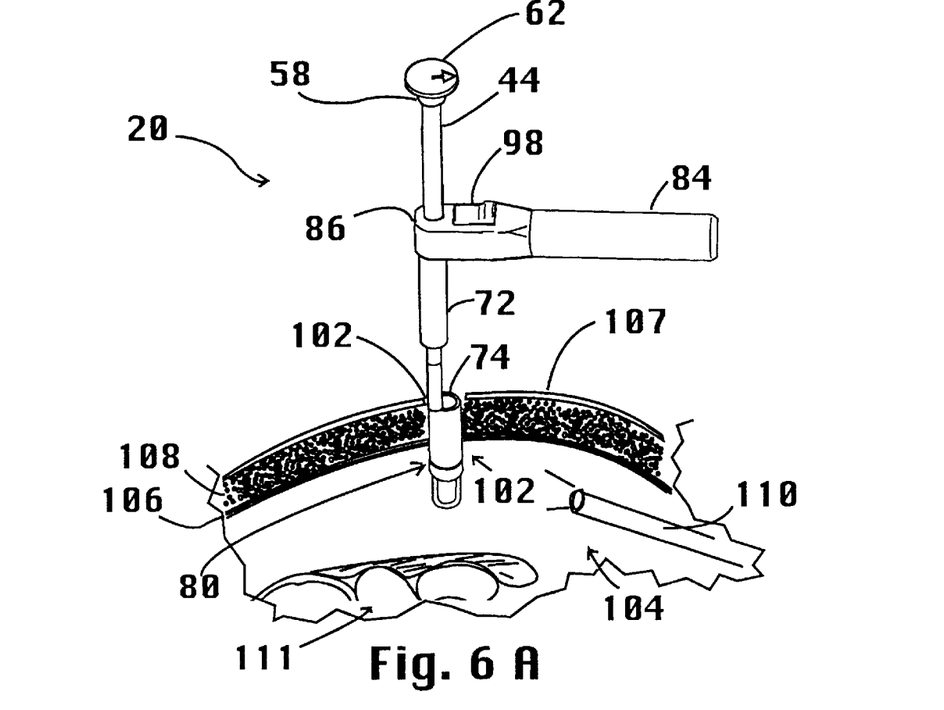
FIGS. 6A–6M show successive steps in suturing an abdominal cannula site incision using the suturing apparatus of FIG. 1.

As a first step, needle 30 of apparatus 20 is sheathed in sheath 82 in the plug. Then, as seen in FIG. 6A, the plug is then inserted into an incision 102 in abdominal wall 106 so that the distal end of the plug extends into the associated abdominal cavity 104. A fat layer 108 is between abdominal wall 106 and the skin 107. The depth of insertion is maintained at an optimum throughout the suturing procedure, by monitoring depth mark 80 with laparoscope 110 from within cavity 104. The laparoscope is also used to prevent any abdominal viscera, shown generally at 111, from being punctured by the reverse needle.

In the second step, key 98 is moved toward the handle to release the needle for axial motion. While apparatus 20 is maintained in the same position with respect to incision 102, knob 58 is pushed toward the incision, as shown by arrow 112 of FIG. 6B, and pin 92 moves along groove section 88b. The result is that the needle is moved from the first (stored) position to the second (withdrawn) position with respect to the plug.

In the third step, the knob is rotated by 180 degrees, as represented by arrow 114 in FIG. 6C, with pin 92 moving along groove section 88c, and thereby moving the needle from the second to the third position with respect to the plug. The user monitors the rotation by observing the position of arrow 62. When the rotation is complete, the pin snaps into deeper groove section 88d. From this third position the knob can only be moved axially away from the incision to the fourth position, as shown in FIG. 6D. It cannot be rotated back to the second position without first using the key to withdraw the pin from deeper groove section 88d.

As mentioned, in the fourth step, the knob is pulled away from the incision according to arrow 116 of FIG. 6D. Pointed end 34 of the needle punctures, near the incision, a small hole in the abdominal wall, while avoiding puncturing the skin, which has been either retracted manually or avoided by suitably tilting apparatus 20 with the upper or proximal end of the plug below the skin surface. During this step, needle 30 is moved from the third to the fourth position. It may be necessary to locate the needle point in fat layer 108. If necessary, the needle may be prevented from falling back into the cavity by pressing a thumb against the plunger. It is preferred that the needle point be long enough to extend above the plug, as shown in FIG. 6D, to allow exposing the needle point above the skin while the plug remains below the skin surface.

In the next step, an ordinary suture 118 is threaded through eye 36 of the needle, as seen in FIG. 6E. It is preferred that the suture is threaded from the side that is away from the shaft, and that an instrument be used to avoid inadvertently puncturing a finger with the needle.

In the sixth step, knob 58 is pushed toward the incision, as represented by arrow 112 in FIG. 6F. Needle 30 is moved back to the third position with respect to the plug by sliding out of the holes it punctured in layers 106 and 108. The needle thus threads the suture through these holes.

In the seventh step, while plug 74 is maintained at the same depth within incision 102, guide handle 84 is rotated around the axis of the shaft according to arrow 120, as seen in FIG. 6G. It will be appreciated that the movement confining means prevents the needle from rotating until it is unlocked by movement of key 98. The needle also rotates within the cavity by remaining at the third position with respect to the plug. Apparatus 20 is thus used also as a device for manipulating the suture within the abdominal cavity.

In the eighth step, the skin is retracted and the knob is pulled away from incision 102, as is indicated by arrow 116 in FIG. 6H. Similar layer puncturing is used, as was described in the fourth step with reference to FIG. 6D. In this instance, the needle point carries suture 118 through the newly punctured holes through layers 106, 108, exposing the suture.

In the ninth step, the suture is unthreaded from eye 36 of the needle, preferably using an instrument 120 to avoid puncturing a finger. This step is shown in FIG. 6I.

In the tenth step, shown in FIG. 6J, the Knob is pushed toward the incision, as represented by arrow 112 and as was described in the sixth step with reference to FIG. 6F. This time the suture is not threaded through the eye, and therefore remains threaded through the holes that have been punctured in the layers.

In the eleventh step, key 98 is used to unlock the shaft for rotation motion, and the knob is rotated according to arrow 122 shown in FIG. 6K The needle is thus brought from the third to the second position with respect to the plug, as verified by orientation arrow 62.

In the twelfth step, knob 58 is pulled away from the incision as indicated by arrow 124, shown in FIG. 6L. Accordingly, the needle moves from the second to the first position with respect to the plug, i.e. into the sheath. A snapping sound confirms that the shaft is locked in place. The laparoscope is used to ascertain that the reverse needle is not trapping any suture or abdominal viscera.

Figure 6M:
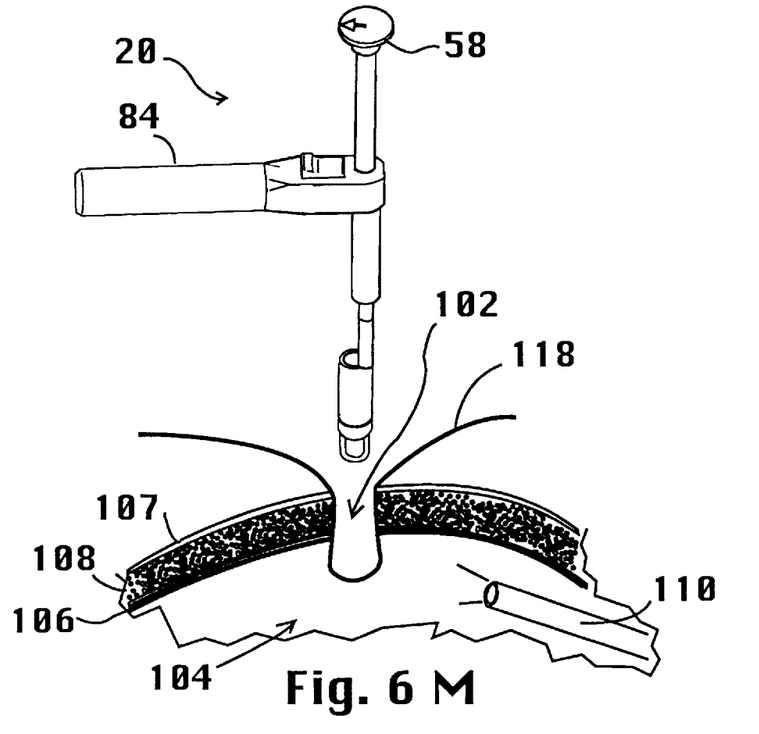

In the thirteenth and final step, the plug and sheathed needle are extracted from incision 102 as seen in FIG. 6M. The ends of the suture are then free for tying together as is known. It is preferred that the apparatus be immediately placed in cold water to facilitate later cleaning, as blood will not have clotted on it.

Suturing apparatus 20 provides a simple yet effective procedure for suturing an abdominal wall incision, and in particular a cannula site incision. The plug serves as a guide for the J-shaped needle, maintaining the position of the needle relative to the incision. The eccentric position of the needle shaft relative to the plug provides for optimal placement of a suture through the abdominal wall. The use of the releasable pin captured in the bilevel groove on the plunger guides the user in transitioning between needle positions.

The plug is generally cylindrical shaped and provides a good seal in the incision for maintaining pneumoperitoneum pressure. The shortness of the plug allows it to be laterally tilted below the skin surface during exposure of the needle tip, avoiding unnecessary trauma to the skin. The plug also functions as a sheath for the needle, providing safe insertion, removal and storage of the apparatus. The apparatus is also readily disassembled for cleaning between procedures and, accordingly, worn parts are easily replaced.

In the above description numerous details have been set forth in order to provide a more thorough understanding of the present invention. It will be obvious, however, to one skilled in the art that the present invention may be practiced without these specific details. In other instances, well known features have not been described in detail in order to not obscure unnecessarily the present invention.

The invention claimed is:

1. A surgical apparatus for use in suturing an incision in an abdominal wall, comprising:
   a J-shaped suture manipulating device including (a) an elongated shaft with a proximal end and a distal end, the proximal end being adapted for manipulating the location and orientation of the distal end, (b) a needle with a base end and a pointed end suitable for puncturing an abdominal wall, the needle adapted for receiving a suture near the pointed end, and (c) a support member for supporting the base end of the needle on the distal end of the shaft in such a way that the needle is laterally spaced from and adjacent to the shaft and the pointed end of the needle points in the general direction of the proximal end of the shaft; and
   a guide element adapted for insertion into an abdominal wall incision, the guide element having a proximal end, a distal end, and a passage extending between the proximal end and the distal end of the guide element, the shaft being slidable axially in the passage for moving the needle relative to the guide element.

2. The apparatus of claim 1, further comprising guide handle means attached to the guide element for manually supporting the guide element.

3. The apparatus of claim 1, further comprising shaft handle means attached to the proximal end of the shaft for manually manipulating the suture manipulating device.

4. The apparatus of claim 1, wherein the guide element includes gauge means for indicating the depth of insertion of the guide element in an incision.

5. The apparatus of claim 1, wherein the guide element has a surface adapted for sealing an incision in which it is placed.

6. The apparatus of claim 1, wherein the shaft is cylindrical and the guide element passage is cylindrical for receiving matingly the shaft, the shaft thereby being capable of being moved axially and rotationally relative to the guide element.

7. The apparatus of claim 6, wherein the guide element has a surface adapted for sealing an incision in which it is placed.

8. The apparatus of claim 6, further comprising guide handle means attached to the guide element for manually manipulating the guide element in an incision.

9. The apparatus of claim 6, further comprising shaft handle means attached to the proximal end of the shaft for manually manipulating the shaft relative to the guide element.

10. The apparatus of claim 9, wherein the shaft handle means includes a knob.

11. The apparatus of claim 6, wherein the guide element includes gauge means for indicating the depth of insertion of the guide element in an incision.

12. The apparatus of claim 6, wherein the guide element defines a sheath for receiving the pointed end of the needle.

13. The apparatus of claim 6, further comprising movement confining means for limiting the range of movement of the shaft relative to the guide element.

14. The apparatus of claim 13, wherein the movement confining means prevents axial movement of the shaft when the shaft is in a given axial position relative to the guide element.

15. The apparatus of claim 13, wherein the movement confining means prevents rotational movement of the shaft when the shaft is in a given rotational position relative to the guide element.

16. The apparatus of claim 15, wherein the movement confining means further limits the range of axial movement of the shaft.

17. The apparatus of claim 6, wherein the guide element is cylindrical.

18. The apparatus of claim 17, wherein the guide element defines a sheath, and wherein the shaft is axially movable to move the pointed end of the needle between a first position in the sheath and a second position outside the sheath and in line with the guide element.

19. The apparatus of claim 17, wherein the passage has a center axis that is spaced from a center axis of the guide element, and the support member is dimensioned in such a way that rotating the shaft moves the needle between a first position in line with the guide element and a second position spaced laterally from the guide element.

20. The apparatus of claim 17, wherein the proximal end of the shaft is axially movable away from the guide element for moving the needle between a first position spaced axially and laterally from the guide element and a second position laterally adjacent to the guide element.

21. The apparatus of claim 20, wherein a portion of the distal end of the guide element is slotted for allowing receipt of the support member therein, when the needle is moved to the second position.

22. The apparatus of claim 17, further comprising movement confining means for limiting the range of movement of the shaft relative to the guide element.

23. A surgical apparatus for use in suturing an incision in an abdominal wall, comprising:

a J-shaped suture manipulating device including (a) an elongated cylindrical shaft with a proximal end and a distal end, (b) a needle with a base end and a pointed end suitable for puncturing an abdominal wall, the needle adapted for receiving a suture near the pointed end, and (c) a support member for supporting the base end of the needle on the distal end of the shaft in such a way that the needle is laterally spaced from and adjacent to the shaft and the pointed end of the needle points in the general direction of the proximal end of the shaft;

a cylindrical guide element adapted for insertion into an abdominal wall incision, the guide element having a proximal end, a distal end, and a cylindrical passage extending between the proximal end and the distal end of the guide element, the passage having a center axis that is offset from a center axis of the guide element, the shaft being matingly and slidingly received in the passage with the distal end of the shaft corresponding to the distal end of the guide element, the shaft thereby being capable of being moved axially and rotationally relative to the guide element, the guide element defining a sheath for receiving the pointed end of the needle;

guide handle means attached to the guide element for manually manipulating the guide element in an incision;

shaft handle means attached to the proximal end of the shaft for manually manipulating the shaft relative to the guide element; and movement confining means for limiting the range of movement of the shaft relative to the guide element.

24. The apparatus of claim 23, wherein the shaft is axially movable to move the pointed end of the needle from a first position in the sheath to a second position outside the sheath and in line with the guide element, and wherein the support member is dimensioned in such a way that rotating the shaft moves the needle from the second position to a third position spaced laterally from the guide element, and wherein the proximal end of the shaft is axially movable away from the guide element for moving the needle from the third position to a fourth position laterally adjacent to the guide element.

25. The apparatus of claim 24, wherein the movement confining means additionally prevents the shaft from rotating once the needle has been moved from the second position to the third position.

26. The apparatus of claim 24, wherein the movement confining means additionally immobilizes the shaft relative to the guide element, when the pointed end of the needle is in the sheath.

27. The apparatus of claim 26, further including an unlocking mechanism connected to the movement confining means for releasing the shaft for axial movement when the pointed end of the needle is in the sheath.

28. The apparatus of claim 24, wherein the pointed end of the needle extends toward the guide handle means beyond the proximal end of the guide element when the needle is in the fourth position for allowing positioning the pointed end of the needle above the skin while the guide element is positioned below the skin.

* * * * *